United States Patent [19]

Riley et al.

[11] Patent Number: 5,055,577

[45] Date of Patent: Oct. 8, 1991

[54] PREPARATION OF URETHANE PRODUCTS

[75] Inventors: Dennis P. Riley, Ballwin; William D. McGhee, St. Louis, both of Mo.

[73] Assignee: Monsanto Company, St. Louis, Mo.

[21] Appl. No.: 539,496

[22] Filed: Jun. 18, 1990

[51] Int. Cl.$^5$ .................. C07D 265/30; C07D 211/06; C07D 207/10; C07C 269/04

[52] U.S. Cl. .................................... 544/172; 546/226; 548/531; 560/27; 560/32; 560/114; 560/157; 560/162

[58] Field of Search .................. 560/27, 32, 114, 157, 560/162; 544/172; 548/531; 546/226

[56] References Cited

U.S. PATENT DOCUMENTS

| | | | |
|---|---|---|---|
| 4,467,089 | 9/1984 | Bechara | 544/351 |
| 4,945,179 | 7/1990 | Drent | 560/114 |

FOREIGN PATENT DOCUMENTS 1275246 12/1986 Japan .................................... 560/114

OTHER PUBLICATIONS

Chemistry Express, vol. 1, No. 4, pp. 224–227 (1986) Kinki Chemical Society, Japan.

*Primary Examiner*—Johann Richter
*Attorney, Agent, or Firm*—Charles E. Smith; Paul L. Passley; James C. Bolding

[57] ABSTRACT

The present invention provides a process for preparing urethanes from primary or secondary amines, carbon dioxide and a diolefin. The amine is reacted with carbon dioxide to form the ammonium carbamate salt which is then reacted with a stoichiometric amount of a diolefin coordinated to palladium(II).

9 Claims, No Drawings

PREPARATION OF URETHANE PRODUCTS

BACKGROUND OF THE INVENTION

1. Field of the Invention

The present invention relates to a new and useful process for preparing new and useful urethanes. More particularly, the present invention relates to a new and useful process for preparing new and useful urethanes from amines, carbon dioxide and a diolefin.

2. Prior Art

Urethanes have been typically synthesized by the reaction of a primary amine with phosgene to form an isocyanate. Thereafter, the isocyanate is reacted with an alcohol to form the corresponding urethane. Phosgene is very toxic and thus requires very careful handling from a product and worker safety standpoint. Preparing urethane products without using phosgene in an economical manner would be an achievement of considerable significance in the art.

U.S. Pat. No. 4,467,089 discloses the preparation of certain carbamic acid derivatives by the simultaneous reaction of a secondary amine and a tertiary amine with carbon dioxide to produce corresponding tertiary amine salts of N-substituted carbamic acid. The secondary and tertiary amines are brought together in equimolar proportions in the presence of excess carbon dioxide under mild conditions. The secondary amine reacts with $CO_2$ in the presence of the tertiary amine to form the corresponding disubstituted tertiary ammonium carbamate salt. The salt is described as being useful as heat activatable delayed action catalysts, especially for use in polyurethane formulations.

In *Chemistry Express*, Vol. 1, No. 4, pp 224-227 (1986), Kinki Chemical Society, Japan, it is disclosed that primary and secondary amines absorb $CO_2$ to form carbamic acid amine salts and that when an equivalent of 1,8-diazabicyclo[5.4.0]undec-7-ene (DBU) is added, additional $CO_2$ is absorbed to form the DBU-carbamate salt. The DBU carbamate salt when reacted with an alkylating agent forms a carbamate ester (urethane). Yield and selectivity of the urethane product are highly dependent on the nature of the alkylating agent. When dibutylamine is reacted with $CO_2$ in the presence of DBU and the resulting DBU-carbamate salt is reacted with butyl chloride as the alkylating agent, a yield of only 17% is realized. With butyl bromide, the yield is 86%.

SUMMARY OF THE INVENTION

The present invention provides a new and useful process for making urethanes of the following general formula:

where $R_1$ and $R_2$ are independently hydrogen, alkyl, cycloalkyl, aryl, aralkyl or alkaryl radicals having 1 to 22 carbon atoms provided that no more than one of $R_1$ and $R_2$ is hydrogen by reacting a suitable primary or secondary amine with carbon dioxide to form the ammonium carbamate salt which is then reacted with a stoichiometric amount of a diolefin coordinated to palladium(II) ($Pd^{+2}$). Optionally, the reaction is carried out with a strongly basic nitrogenous base. $R_1$ and $R_2$ together with the nitrogen may be bound to form saturated or unsaturated heterocyclic 5 to 9 membered ring radicals, such as morpholino, pyrrolidino, piperidino, etc. $R_3$ is a residue of the coupling of the diolefin and the carbamate ion.

The stoichiometric system of the present invention is based on nucleophilic attack of carbamate anions premade from $CO_2$ and a primary amine or secondary amine or mixture thereof on a palladium(II) activated diolefin. Reductive cleavage of the palladium(II) yields the urethane product. Products made in accordance with the present invention are useful as intermediates in agricultural chemicals, such as carbamate insecticides and herbicides, and in specialty chemical applications.

DETAILED DESCRIPTION OF THE INVENTION

The urethanes are prepared in accordance with the present invention by bringing into reactive contact either a suitable secondary amine or a suitable primary amine or mixture of such amines and carbon dioxide in a confined zone, such as a reactor, to prepare the corresponding ammonium carbamate salt. Preferably the amine is in solution and the carbon dioxide is bubbled through the solution. The reaction proceeds without the need of elevated pressure or temperatures in a slightly exothermic reaction to give the alkyl ammonium salt of the corresponding carbamate anion. In some cases the use of a stoichiometric amount of a tertiary amine during the reaction of the primary or secondary amine and carbon dioxide provides improved yields of the desired urethane product.

The reaction proceeds using stoichiometric amounts of the reactants. A palladium(II)-dihalodiolefin complex is prepared and brought into reactive contact with either a solution of the ammonium carbamate salt or in a slurry of the ammonium carbamate salt. The carbamate anion attacks the diolefin coordinated to palladium(II) in a nucleophilic fashion. The resulting palladium(II) alkylurethane complex is then treated with a suitable reducing agent. The reductive cleavage results in the formation of the desired urethanes in excellent yields. The urethanes are recovered in a conventional manner from the reaction.

The alkyl ammonium salt of the corresponding carbamate anion may be prepared in solution in the presence or not in the presence of a strong base, such as strong organic bases. The use of a strong base shifts the equilibrium toward the production of the carbamate anions. Where the reaction between the primary or secondary amine is carried out in the presence of a base, the reaction may be represented by the equation (I). The resulting ammonium carbamate salt solutions are normally homogeneous.

Where the reaction between the primary or secondary amine is carried out in the absence of an added strong base, the reaction may be represented by equation (2):

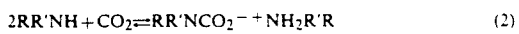

Equation (3) shows the results of the addition of a $PdCl_2$(diolefin) complex to the carbamate salt solution of equation (1) in the presence of sodium borohydride, a suitable reducing agent:

$$RR'NCO_2^- \ HBase^+ + PdCl_2(\text{diolefin}) \xrightarrow{NaBH_4} \quad (3)$$

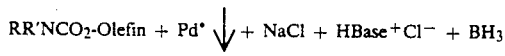

$$RR'NCO_2\text{-Olefin} + Pd^\bullet \downarrow + NaCl + HBase^+Cl^- + BH_3$$

Equation (4) shows the results of the addition of (dicyclopentadiene)palladium dichloride to a premade solution of carbamate salts.

$$RR'NCO_2^- \ HBase^+ + (\text{dicyclopentadiene})PdCl_2 \xrightarrow{NaBH_4} \quad (4)$$

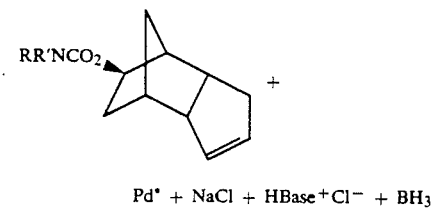

$$Pd^\bullet + NaCl + HBase^+Cl^- + BH_3$$

Normally, the reaction proceeds smoothly at $-5°$ C. and under an atmosphere of carbon dioxide. The reaction is virtually instantaneous as the yellow-orange color of the palladium complex decolorizes upon addition thereof to the carbamate solution. The addition of the reducing agent and aqueous sodium hydroxide solution gives the carbamate esters in a good isolated yield. The palladium precipitates and is thereafter separated.

In accordance with another aspect of the present invention, a stabilizing reagent may be added prior to the addition of the reducing agent to the intermediate carbamate-palladium complex. In the case of the norbornadiene palladium chloride complex, addition of a stabilizing agent results in higher selectivity of the desired urethane product as depicted in equation (5) below.

A preferred intermediate stabilizing agent is 1,2- bis(-diphenylphosphino)ethane (DIPHOS). Addition of the carbamate salt solution to palladium(dichloride) (norbornadiene) complex at $-78°$ C. followed by warming to about $5°$ C. under a carbon dioxide atmosphere gives a light yellow solution. Addition of DIPHOS followed by sodium borohydride in aqueous 2.5N NaOH gives a clear solution and a black precipitate (Pd°). The use of the stabilizer is illustrated by equation (5):

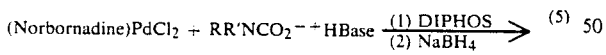

$$(\text{Norbornadine})PdCl_2 + RR'NCO_2^{-+}HBase \xrightarrow[(2)\ NaBH_4]{(1)\ DIPHOS} \quad (5)$$

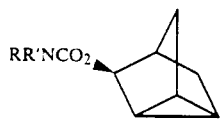

The primary or secondary amine used to prepare the carbamate esters in accordance with the present invention may be represented by the following chemical structure:

$$R_1R_2NH$$

where $R_1$ and $R_2$ independently represent hydrogen or alkyl, cycloalkyl, aryl, aralkyl or alkaryl radicals having 1 to 22 carbon atoms with the proviso that only one of $R_1$ and $R_2$ may be a hydrogen. The alkyls, cycloalkyls, aryls, aralkyls or alkaryls can be straight-chained or branched, including methyl, ethyl, n-propyl, isopropyl, n-butyl, isobutyl, t-butyl, n-pentyl, isopentyl, n-hexyl, n-octyl, phenyl, benzyl, etc.

The primary or secondary amine reacts with $CO_2$ to reversibly form the corresponding ammonium carbamate salt. To shift the equilibrium reaction move favorably to the ammonium carbamate salt, a strongly basic nitrogen containing base can be added. Such nitrogen bases include tertiary amines (e g., triethylamine, diisopropylethylamine, quinuclidene, etc.), amidines (e.g., DBU, 1,8-diazabicyclo[5.4.0]undec-7-ene, etc.) and quanidines (e.g., tetramethylguanidine, tetraethylguanidine, etc.).

An advantage of the present process is that the reaction between the primary or secondary amines and $CO_2$ proceeds under mild temperature and pressure. Room temperature and a pressure of one atmosphere is suitable. The reaction preferably is carried out between $-78°$ C. and room temperature under a $CO_2$ pressure in the range of 0.1 atmosphere to supercritical pressure.

The diolefins coordinated to a palladium(II), and the ammonium carbamate salts are brought into reactive contact under conditions such that the coordinated diolefin undergoes nucleophilic attack from the carbamate anion. The preferred diolefins include dicyclopentadiene, norbornadiene, and 1,5 cyclooctadiene and are depicted in structures 1-3, respectively.

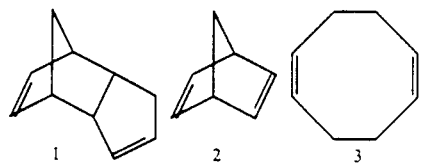

The palladium is reductively cleaved from the reaction product of the carbamic acid-amine salt by the use of a reducing agent such as $NaBH_4$, hydrogen gas and the like. A preferred reducing agent is sodium borohydride. The cleavage results in the palladium being precipitated in free metal form.

The reaction is carried out in a suitable organic solvent, among which are tetrahydrofuran, 1,2-dimethoxyethane, and other ether and polyether solvents, as well as methylene chloride, 1,2-dichloroethane and other chlorinated solvents.

In the working examples, the use of dicyclopentadiene, norbornadiene and cyclooctadiene as the diolefin coupled to palladium is illustrated.

The invention will now be further disclosed in the following illustrated examples wherein parts and percentages are given on a molar basis unless otherwise specified.

EXAMPLE 1

In a 3-neck 500mL round bottomed flask was added 720 mg of n-butyl amine and 20 mL methylene chloride. The flask was fitted with an addition funnel, a gas inlet and a rubber stopper. The clear solution was cooled to $0°$ C. and carbon dioxide was bubbled through the solution.

In a glass vial was weighed 496 mg of dicyclopentadiene palladium dichloride and 195 mg of dodecane (as an internal standard for GC analysis). To this was added 25 mL methylene chloride and the resulting orange solution was transferred to the addition funnel.

After 15 min of $CO_2$ addition, the palladium complex was added dropwise to the carbamate solution over a 30 min period. Upon addition, the palladium solution decolorized. After addition was complete the reaction mixture was stirred at 0° C. for 15 min. The reaction was quenched by bubbling hydrogen through the solution. The reaction was allowed to warm to room temperature with the continuous addition of hydrogen during which time the reaction slowly deposited a black precipitate. After 1.5 h the reaction mixture was filtered through celite using methylene chloride to wash the celite. A G.C. trace of the clear filtrate was taken (100%). The crude filtrate was washed with 1×50 mL $H_2O$, 1×100 mL 0.6M HCl, and 1×50 mL $H_2O$. The aqueous washes were each extracted with 1×50 mL methylene chloride. The combined organic layers were dried over sodium carbonate, filtered and then concentrated leaving an oily residue. This residue was chromatographed on silica gel using 50% methylene chloride/hexane (TLC plates developed using phosphomolybdic acid). Upon concentration of the desired fractions 285 mg (72%) of the urethane was isolated as a white solid.

EXAMPLE 2

In a 3-neck 500 mL round bottomed flask was added 700 mg of sec-butyl amine and 20 mL methylene chloride. The flask was fitted with an addition funnel, a gas inlet and a rubber stopper. The clear solution was cooled to 0° C. and carbon dioxide was bubbled through the solution. In a glass vial was weighed 500 mg of dicyclopentadiene palladium dichloride and 218 mg of dodecane (internal standard for GC analysis). To this was added 25 mL methylene chloride and the resulting orange solution was transferred to the addition funnel.

After 15 min of $CO_2$ addition, the palladium complex was added dropwise to the carbamate solution over a 30 min period. Upon addition, the palladium solution decolorized. After addition was complete the reaction mixture was stirred at 0° C. for 15 min. The reaction was quenched by adding 480 mg of $NaBH_4$ in 2 mL 2.5N NaOH to the solution. The reaction was allowed to sit at 0° C. for 10 min during which time the formation of a black ppt occurred. The reaction mixture was filtered through celite using methylene chloride to wash the celite. A G.C. trace of the clear filtrate was taken (69%). The crude filtrate was washed with 1×50 mL $H_2O$, 1×100 mL 0.6M HCl, and 1×50 mL $H_2O$. The aqueous washes were each extracted with 1×50 mL methylene chloride. The combined organic layers were dried over sodium carbonate, filtered and then concentrated leaving an oily residue. This residue was chromatographed on silica gel using 50% methylene chloride/hexane (TLC plates developed using phosphomolybdic acid). Upon concentration of the desired fractions 164 mg [41%] of the urethane was isolated as a white solid.

EXAMPLE 3

In a Fischer-Porter bottle was added 700 mg of t-butyl amine and 20 mL methylene chloride. The bottle was attached to the pressure apparatus. The clear solution was cooled to −5° C. and 80 psi carbon dioxide solution was added above the solution (the carbamate salt came out of solution).

In a second Fischer-Porter bottle was weighed 526 mg of dicyclopentadiene palladium dichloride and 213 mg dodecane (as internal standard for G.C. analysis). To this was added 25 mL methylene chloride.

After 30 min of $CO_2$ addition, the orange solution of the palladium complex was forced into the carbamate slurry using carbon dioxide pressure. Upon addition the palladium solution darkened slightly (some palladium reduction). After addition was complete the reaction mixture was stirred at 0° C. for 15 min. after which time the pressure was released and the solution transferred to a 250 mL round bottomed flask. The flask was cooled to 0° C. and then the reaction was quenched by the addition of 475 mg of $NaBH_4$ in 2 mL 2.5N NaOH to the solution. The reaction was allowed to sit at 0° C. for 10 min during which time the formation of a black ppt occurred. The reaction mixture was filtered through celite using methylene chloride to wash the celite. The crude filtrate was washed with 1×50 mL $H_2O$, 2×100 mL 0.6M HCl, and 1×50 mL $H_2O$. The aqueous washes were each extracted with 1×50 mL methylene chloride. The combined organic layers were dried over sodium carbonate, filtered and then concentrated leaving an oily residue. This residue was chromatographed on silica gel using 50% methylene chloride/hexane (TLC plates developed using phosphomolybdic acid). Upon concentration of the desired fractions 109 mg (26%) of the urethane product was isolated as a white solid.

EXAMPLE 4

In a 3-neck 500 mL round bottomed flask was added 425 mg of morpholine, 611 mg of 1,5-diazabioyclo [4.3.0]non-5-ene (DBN) and 20 mL methylene chloride. The flask was fitted with an addition funnel, a gas inlet and a rubber stopper. The clear solution was cooled to −5° C. and carbon dioxide was bubbled through the solution.

In a glass vial was weighed 487 mg of dicyclopentadiene palladium dichloride. To this was added 25 mL methylene chloride and the resulting orange solution was transferred to the addition funnel.

After 15 min. of $CO_2$ addition, the palladium complex was added dropwise to the carbamate solution over a 30 min period. Upon addition, the palladium solution darkened slightly (some palladium reduction). After addition was complete the reaction mixture was stirred at 0° C. for 15 min. The reaction was quenched by the addition of 502 mg of $NaBH_4$ in 2 mL 2.5N NaOH to the solution. The reaction was allowed to sit at 0° C. for 10 min during which time the formation of a black ppt occurred. The reaction mixture was filtered through celite using methylene chloride to wash the celite. The crude filtrate was washed with 1×50 mL $H_2O$, 2×100 mL 0.6M HCl, and 1×50 mL $H_2O$. The aqueous washes were each extracted with 1×50 mL methylene chloride. The combined organic layers were dried over sodium carbonate, filtered and then concentrated leaving an oily residue. This residue was chromatographed on silica gel using 20% diethyl ether/hexane (TLC plates developed using phosphomolybdic acid). Upon concentration of the desired fractions 222 mg (54%) of the urethane product was isolated as a clear oil which slowly solidified in the freezer.

EXAMPLE 5

In a Fischer-Porter bottle was added 542 mg of aniline, 754 mg of (i-Pr)$_2$Net and 20 mL methylene chloride. The bottle was attached to the pressure apparatus. The clear solution was cooled to −5° C. and 80 psi carbon dioxide was added above the solution.

In a second Fischer-Porter bottle was weighed 506 mg of dicyclopentadiene palladium dichloride and to this was added 25 mL methylene chloride.

After 30 min of $CO_2$ addition, the palladium complex was forced into the carbamate slurry using carbon dioxide pressure. Upon addition the palladium solution darkened slightly (some palladium reduction). After addition was complete the reaction mixture was stirred at 0° C. for 15 min after which time the pressure was released and the solution transferred to a 250mL round bottomed flask. The flask was cooled to 0° C. and then the reaction was quenched by the addition of 500 mg of $NaBH_4$ in 2 mL 2.5N NaOH to the solution. The reaction was allowed to sit at 0° C. for 10 min. during which time formation of a black ppt occurred. The reaction mixture was filtered through celite using methylene chloride to wash the celite. The crude filtrate was washed with $1 \times 50$ mL $H_2O$, $2 \times 100$ mL 0.6M HCl, and $1 \times 50$ mL $H_2O$. The aqueous washes were each extracted with $1 \times 50$ mL methylene chloride. The combined organic layers were dried over sodium carbonate, filtered and then concentrated leaving an oily residue. This residue was chromatographed on silica gel using 50% methylene chloride/hexane (TLC plates developed using phosphomolybdic acid). Upon concentration of the desired fractions 127 mg (29%) of the urethane was isolated as a white solid.

EXAMPLE 6

In a 500 mL 3-neck flask was weighed 500 mg of norbornadiene palladium dichloride. The flask was fitted with an addition funnel, a gas inlet and a rubber septa. The apparatus was pump-filled with nitrogen followed by the addition of 30 mL dry THF and 144 mg of dodecane (as internal standard for GC analysis). This yellow slurry was cooled to −78° C. using a dry ice /IPA bath.

In a 50 mL round bottomed flask was weighed 800 mg benzyl amine and 880 mg of quinuclidene. To this was added 15 mL dry THF followed by the addition of carbon dioxide. The clear solution was cooled to 0° C. and $CO_2$ was bubbled through the solution for 15 min. At the end of this time a small amount of solid had appeared. The carbamate slurry was added to the palladium(II) complex at −78° C. After addition was complete the reaction mixture was warmed to 0° C. (ice bath) and was allowed to stir for 6 h at 0° C. Thereafter, a solution of 760 mg of 1,2 bis(diphenylphosphino)ethane (DIPHOS) in 10 mL THF was added and the ice bath removed. The resulting reaction mixture was allowed to sit overnight at room temperature. To the reaction mixture 570 mg of $NaBH_4$ in 1 mL NaOH and 10 mL THF was added giving a black suspension. The reaction mixture was allowed to stir at RT for h and was then filtered through celite using THF to wash the celite. The clear filtrate was concentrated leaving an oily residue. By G.C. a yield of 80% was calculated.

The crude product was chromatographed on silica gel using 44% $CH_2Cl_2$/hexane. Upon concentration of the desired fractions 235 mg (52%) of the urethane was obtained as a white solid.

EXAMPLE 7

In a 3-neck 500 mL round bottomed flask was added 1.115 g of n-butyl amine and 40 mL methylene chloride. The flask was fitted with an addition funnel, a gas inlet and a rubber stopper. The clear solution was cooled to −35° C. and carbon dioxide was bubbled through the solution.

In a glass vial was weighed 755 mg of 1,5cyclooctadiene palladium dichloride. To this was added 30 mL methylene chloride and the resulting yellow-orange solution was added to the addition funnel.

After 15 min of $CO_2$ addition, the palladium complex was added dropwise to the carbamate slurry over a 30 min period. Upon addition, the palladium solution decolorized. After addition was complete the reaction mixture was stirred at −35° C. for 15 min. The reaction was quenched by the addition of 760 mg of $NaBH_4$ in 2 mL 2.5N NaOH to the solution. The reaction was allowed to sit at −35° C. for 10 min during which time the formation of a black ppt occurred. The reaction mixture was filtered through celite using methylene chloride to wash the celite. The crude filtrate was washed with $1 \times 50$ mL $H_2O$, $2 \times 100$ mL 0.6M HCl, and $1 \times 50$ mL $H_2O$. The aqueous washes were each extracted with $1 \times 50$ mL methylene chloride. The combined organic layers were dried over sodium carbonate, filtered and then concentrated leaving an oily residue. This residue was chromatographed on silica gel using 50% methylene chloride/hexane (TLC plates developed using phosphomolybdic acid). Upon concentration of the desired fractions 96 mg (16%) of the urethane was obtained as a clear oil.

The reactions using dicyclopentadiene, norbornadiene and 1,5-cyclooctadiene in the above Examples may be depicted by the equations (6)−(8):

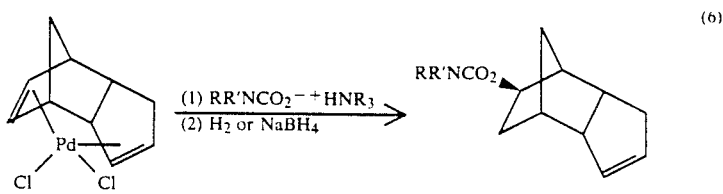

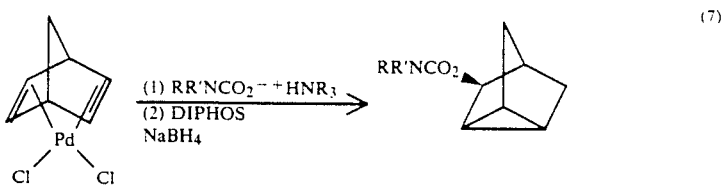

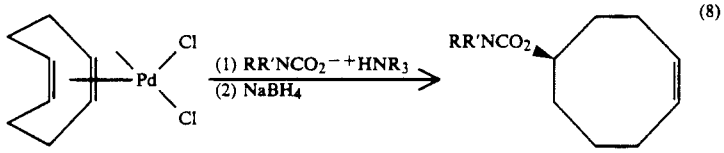

In Table 1 yield data have been set forth where palladium dichloro(dicyclopentadiene) was reacted with a variety of carbamate salts using $NaBH_4$ or $H_2$ as the reducing agent. All reactions were carried out at $-5°$ C. using methylene chloride as the solvent. Reaction time was 15-30 min after addition of the olefin complex was complete. All reactions were carried out under an atmosphere of $CO_2$ unless otherwise indicated. GC yields refer to yields using gas chromatographic analysis with dodecane as an internal standard. The abbreviation DBN refers to 1,5-diazabicyclo[4.3.0]non-5-ene.

TABLE 1

| CARBAMATE SALT | G.C. Yield (%) $NaBH_4$ | G.C. Yield (%) $H_2$ | Isolated Yield (%) |
|---|---|---|---|
| n-BuNHCO$_2^-$ $^+$H$_3$N(n-Bu) | 89-100 | 94-100 | 72 |
| sec-BuNHCO$_2^-$ $^+$H$_3$N(s-Bu) | 69 | — | 41 |
| tert-BuNHCO$_2^-$ $^+$H$_3$N(t-Bu) | 54 | — | — |
| tert-BuNHCO$_2^-$ $^+$H$_3$N(t-Bu)* | 80 | — | 26 |
| tert-BuNHCO$_2^-$ $^+$HDBN | 60 | — | — |
| PhCH$_2$NHCO$_2^-$ $^+$H$_3$NCH$_2$Ph | 67-83 | — | 54 |
| PhCH$_2$NHCO$_2^-$ $^+$HDBN | 68 | 72 | — |
| CH(CH$_2$CH$_2$)$_2$NCO$_2^-$ $^+$H$_2$N(CH$_2$CH$_2$)$_2$CH | 55 | — | 20 |
| CH(CH$_2$CH$_2$)$_2$NCO$_2^-$ $^+$HDBN | 48-53 | — | — |
| O(CH$_2$CH$_2$)$_2$NCO$_2^-$ $^+$H$_2$N(CH$_2$CH$_2$)$_2$O | 27 | — | — |
| O(CH$_2$CH$_2$)$_2$NCO$_2^-$ $^+$HDBN | 77-79 | 65 | 54 |
| Et$_2$NCO$_2^-$ $^+$H$_2$NEt$_2$ | 44 | 40 | 28 |
| Et$_2$NCO$_2^-$ $^+$HDBN | 53 | — | — |
| PhCH$_2$(Me)NCO$_2^-$ $^+$H$_2$N(Me)CH$_2$Ph | 40 | — | — |
| PhCH$_2$(Me)NCO$_2^-$ $^+$HDBN | 64-82.5 | — | 37 |
| PHNHCO$_2^-$ $^+$H$_3$NPh* | 0 | — | — |
| PhNHCO$_2^-$ $^+$HDBN* | 47 | — | — |
| PhNHCO$_2^-$ $^+$HNEt(i-Pr)$_2$* | 70.5 | — | 29 |

*Under 5 atmospheres of $CO_2$ pressure

In Table 2 yield data have been set forth where norbornadiene palladium dichloride was reacted with a variety of carbamate salts using $NaBH_4$ as the reducing agent. All reactions were carried out at one atmosphere of $CO_2$ pressure using methylene dichloride as a solvent unless otherwise indicated. The carbamate salt was added to the palladium complex at $-78°$ and after addition the reaction was warmed to $-5°$ C. G.C. yields refer to yields using gas chromatographic analysis with dodecane used as the internal standard. The abbreviation DBN refers to 1.5 diazabicyclo[4.3.0]non-5-ene.

TABLE 2

| CARBAMATE SALT | G.C. Yield(%) | Isolated Yield(%) |
|---|---|---|
| n-BuNHCO$_2^-$ $^+$H$_3$N(n-Bu) | 87 | 48 |
| PhCH$_2$NHCO$_2^-$ $^+$H$_3$NCH$_2$Ph | 55 | — |
| PhCH$_2$NHCO$_2^-$ $^+$HDBN | 90 | — |
| PhCH$_2$NHCO$_2^-$ $^+$HQuinuclidine* | 88 | 56 |
| PhCH$_2$(Me)NCO$_2^-$ $^+$H$_2$N(Me)CH$_2$Ph | 8 | — |
| PhCH$_2$(Me)NCO$_2^-$ $^+$HDBN | 100 | 48 |
| PhCH$_2$(Me)NCO$_2^-$ $^+$HQuinuclidene* | 99.5 | — |
| O(CH$_2$CH$_2$)$_2$NCO$_2^-$ $^+$HDBN | 75 | 56.5 |

*Reaction ran in tetrahydrofuran (THF)

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A process of preparing a urethane of the following formula:

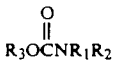

$$R_3OCNR_1R_2$$

wherein $R_1$ and $R_2$ are independently hydrogen or alkyl, cycloalkyl, aryl, aralkyl or alkaryl radicals having 1 to 22 carbon atoms, provided that both $R_1$ and $R_2$ are not hydrogen, or wherein $R_1$ and $R_2$ together with the nitrogen may be bound to form a heterocyclic 5 to 9 membered ring radical, and $R_3$ is a monoolefin comprising the steps of:
   (a) bringing $CO_2$ and a primary amine or secondary amine into reactive contact, optionally in the presence of a strongly basic nitrogenous compound, in a solvent to form the corresponding ammonium carbamate salt,
   (b) reacting said carbamate salt with a diolefin complex of palladium(II), and
   (c) reducing the produce of Step (b) with a reducing agent to cleave the palladium from the complex to produce said urethane and palladium metal.

2. The process of claim 1 wherein the diolefin is complexed with a palladium(II) dihalide salt.

3. The process of claim 2 wherein the halide is palladium(II) dichloride salt.

4. The process of claim 1 wherein the reducing agent is a borohydride of an alkali metal.

5. The process of claim 1 wherein the diolefin is dicyclopentadiene, norbornadiene, or 1,5-cyclooctadiene.

6. The process of claim 5 wherein the diolefin is dicyclopentadiene.

7. The process of claim 1 wherein the reducing agent is $H_2$.

8. The process of claim 1 wherein the solvent is methylene chloride or tetrahydrofuran.

9. The process of claim 1 wherein the reaction is carried out in the presence of a strongly basic nitrogenous compound which is a tertiary amine, amidine or guanidine.

* * * * *